United States Patent
Walter et al.

(10) Patent No.: US 12,377,225 B2
(45) Date of Patent: Aug. 5, 2025

(54) INJECTION DEVICE WITH EXTRACTION MECHANISM AND ASSOCIATED PROCESS

(71) Applicant: VYGON, Écouen (FR)

(72) Inventors: Thomas Walter, Rueil-Malmaison (FR); Léa Carpentier, Beauvais (FR)

(73) Assignee: VYGON, Écouen (FR)

( * ) Notice: Subject to any disclaimer, the term of this patent is extended or adjusted under 35 U.S.C. 154(b) by 811 days.

(21) Appl. No.: 17/698,831

(22) Filed: Mar. 18, 2022

(65) Prior Publication Data

US 2022/0296820 A1 Sep. 22, 2022

(30) Foreign Application Priority Data

Mar. 19, 2021 (FR) ...................................... 21 02784

(51) Int. Cl.
*A61M 5/32* (2006.01)
*A61M 5/00* (2006.01)
*A61M 5/158* (2006.01)
*A61M 5/315* (2006.01)

(52) U.S. Cl.
CPC ...... *A61M 5/3205* (2013.01); *A61M 5/31511* (2013.01); *A61M 5/008* (2013.01); *A61M 2005/1581* (2013.01); *A61M 2005/1583* (2013.01)

(58) Field of Classification Search
CPC ........ A61M 5/3205; A61M 2005/1581; A61M 2005/1583; A61M 5/008
See application file for complete search history.

(56) References Cited

U.S. PATENT DOCUMENTS

| 2005/0049553 A1 | 3/2005 | Triplett et al. |
| 2005/0059553 A1 | 3/2005 | Misselbrook |
| 2005/0107748 A1 | 5/2005 | Thorne et al. |
| 2011/0178478 A1* | 7/2011 | Huet ................. A61M 39/0208 604/288.04 |

FOREIGN PATENT DOCUMENTS

FR 2 869 806 11/2005

OTHER PUBLICATIONS

Search Report for FR Application No. 2102784 dated Nov. 24, 2021, 2 pages.

\* cited by examiner

*Primary Examiner* — Bradley J Osinski
(74) *Attorney, Agent, or Firm* — NIXON & VANDERHYE

(57) ABSTRACT

Disclosed is an injection device including: —a needle support; —an injection needle integral with the needle support and having a free end arranged away from the needle support; and —a needle extraction mechanism including a base connected to the needle support and a plunger movable relative to the base between a needle use position and a needle extraction position. The base is movable relative to the needle support between an inactive position of the extraction mechanism and an active position of the extraction mechanism. The plunger includes an outer member and an inner member, movable relative to the outer member, from a retracted plunger configuration to a deployed plunger configuration wherein the plunger length is greater than in the retracted configuration.

12 Claims, 8 Drawing Sheets

INJECTION DEVICE WITH EXTRACTION MECHANISM AND ASSOCIATED PROCESS

This application claims priority to FR Patent Application No. 21 02784 filed Mar. 19, 2021, the entire contents of which are hereby incorporated by reference.

BACKGROUND OF THE INVENTION

The present invention relates to an injection device comprising:
- a needle support;
- an injection needle integral with the needle support and having a free end arranged away from the needle support; and
- a mechanism for extracting the injection needle comprising a base connected to the needle support and a plunger movable relative to the base between a needle use position and a needle extraction position, the base being movable relative to the needle support between an inactive and an active extraction mechanism position.

The present invention also relates to a preparation process for such a device and an injection method.

Such a device is used in treating certain pathologies for which it is necessary to regularly inject a liquid drug dosage directly into a patient's organ.

To do so, it is known to permanently implant a chamber under the skin on the patient's chest. This chamber is extended by a tube running through the support to the organ where the drug dosage is to be delivered. The implantable chamber has a reservoir with a perforable cover along its surface in contact with the skin.

To inject the drug dosage, the needle of the device is inserted through the patient's skin into the implantable chamber and the drug dosage is injected into the chamber through the needle.

To remove the needle from the implantable chamber, the practitioner grasps the device holder and pulls the needle out of the chamber.

However, because the membrane of the implantable chamber is relatively strong, a significant pulling force must be exerted on the needle to make it possible to remove it.

To prevent the patient from suffering from the forces exerted on the skin by the implantable chamber during needle removal, it is known to use an injection device equipped with an in situ extraction mechanism as described in FR-2869806.

Such a device is equipped with a mechanical extraction mechanism, mounted on the needle support of the injection device, comprising a plunger making it possible for the practitioner to simply extract the needle, in a continuous and safe manner. For this purpose, the needle held by a holder is gradually swallowed into the plunger during extraction.

The extraction mechanism is hinged to the needle support, so that it can assume an extended position along the patient's body when the mechanism is not in use, in order to reduce the size of the extraction device. To reduce movement of the extraction mechanism, the extraction mechanism is retained in an extended position by a flexible interlocking mechanism.

This device can be further improved. The extraction device has a significant footprint, even in the extended position, that should be reduced. A bulky device is more likely to be the cause of handling errors, such as accidental shocks to the device that are painful for the patient because of the needle implanted in his or her skin.

In addition, disengaging the flexible interlocking mechanism to extract the needle may generate unpleasant jolts when the needle is inserted into the patient's body.

SUMMARY OF THE INVENTION

An object of the invention is therefore to provide an injection device that is less cumbersome and the handling thereof is more comfortable for the patient.

To this end, it is an object of the invention to provide an injection device of the aforementioned type, characterized in that the plunger comprises an outer part and an inner part, movable relative to the outer part, from a retracted plunger configuration to a deployed plunger configuration in which the length of the plunger is greater than in the retracted configuration.

According to particular embodiments, the device according to the invention comprises one or more of the following features, taken alone or in any technically feasible combination:
- the inner member is mounted slidably in an inner passage of the outer member;
- the plunger comprises an flexible interlocking mechanism, adapted to lock the inner member in relation to the outer member when the plunger is deployed;
- the flexible interlocking mechanism comprises at least one snap-in tab held by either the inner or the outer member and at least one housing defined by the other of the inner or outer member, the snap-in tab having a tooth received in the housing when the plunger is deployed;
- the or each housing is located near a first end of the other of the inner or outer member so as to receive one of the teeth when the plunger is deployed, the snap-in mechanism further comprising at least a second housing located near a second end of the other of the inner or outer member so as to receive the tooth when the plunger is retracted;
- the flexible interlocking mechanism comprises at least one ramp extending over the other of the inner member or outer member, the ramp delimiting one of the housings at its upper end, the snap-in tab bearing on the ramp when the plunger moves from the retracted configuration to the deployed configuration;
- the flexible interlocking mechanism is suitable for temporarily holding the inner member relative to the outer member when the plunger is in the retracted configuration;
- in the deployed configuration, the plunger defines an internal space for receiving the needle;
- the device comprises an assembly for temporarily immobilizing the base in the inactive position, which is active when the plunger is in the retracted configuration and deactivated when the plunger passes from the retracted configuration to the deployed configuration;
- the temporary immobilization assembly comprises a first slot extending on the inner member and a second slot, wider than the first slot, extending on the outer member, the first and second slots being oriented toward the needle support, the temporary immobilization assembly further comprising a bar, adapted to engage the first and second slots, the bar having a length greater than the width of the first slot and less than the width of the second slot;
- the inner and outer members have substantially rectangular cross-sections, advantageously comprising rounded corners;

the base is mounted so as to be pivotable on the needle support about a pivot axis, between a position in which the needle is in use and a position in which the needle is extracted;

the pivot axis is perpendicular to a longitudinal axis of the plunger, in particular to a sliding axis of the inner member in relation to the outer member;

either the needle support or the base comprises a pin for guiding the pivoting of the base in relation to the needle support, the other of the needle support and the base defining a joint hole receiving the pin;

in the needle extraction position, the main section of the needle extends completely inside the internal receiving space defined by the plunger;

the needle has the main section on the side of its free end;

the main section defines the free end of the needle;

the needle forms an elbow extended on the side of the free end by a main section extending along an elevation axis and on the side opposite the free end by a connecting section, extending along a longitudinal axis of the plunger.

The invention also has as its object a method for preparing the removal of a needle previously introduced into the body of a patient, implemented prior to removal of the needle, comprising the following steps:

providing a device as described above, with the extraction mechanism in its inactive position and the plunger in its retracted configuration;

moving the inner member relative to the outer member to move the plunger from its retracted configuration to its deployed configuration, increasing the length of the plunger;

moving the base from the inactive position to the active position of the extraction mechanism.

It is a further object of the invention to provide an injection method comprising the following steps:

providing a device as described above;

introducing the needle into the patient's body, the tip piercing a cover of an implantable chamber; and injecting a drug solution through the needle into the implantable chamber;

preparing for removal of the needle by the method as described above;

removing the needle by moving the plunger from the needle use position to the needle removal position;

The method according to the invention may comprise one or more of the following features, taken alone or in any technically possible combination:

movement of the internal member causes deactivation of a temporary immobilization mechanism of the base, making movement thereof possible;

the main section of the needle extends entirely inside the plunger after the needle has been removed.

DESCRIPTION OF THE DRAWINGS

The invention will be better understood upon reading the following description, given only by way of example and made with reference to the appended drawings, of which.

DETAILED DESCRIPTION OF THE INVENTION

Figure 1:
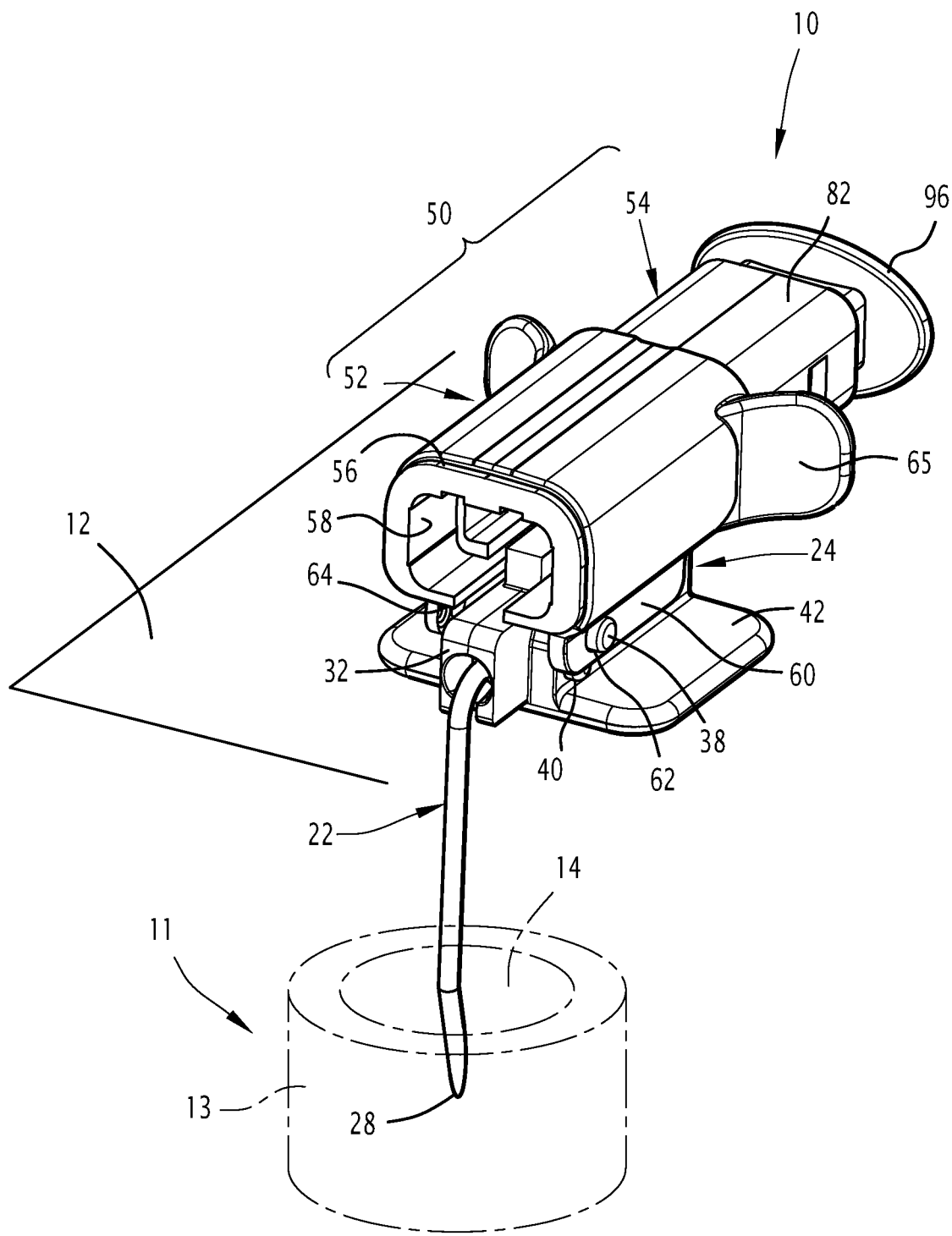
FIG. 1 is a three-quarter perspective view of an injection device according to the invention, in a needle usage configuration.

In FIGS. 1 to 8 is shown an injection device 10 according to the invention. The device 10 is intended to be connected to an implantable chamber 11 (shown schematically in FIG. 1) for injecting a drug solution therein.

As known per se, the implantable chamber 11 is placed under a patient's skin 12. This chamber 11 has a generally cylindrical reservoir 13, delimited by a perforable membrane 14 on its face in contact with the inner surface of the skin. The reservoir is connected to a tube (not shown) for delivering the drug solution to an organ where a drug dosage is to be delivered.

The injection device 10 comprises a needle 22 integral with a needle support 24, extended by a tubing connected to the needle and fixed, glued in particular, to the needle support 24. It comprises a needle 22 extraction mechanism 50 carried by the needle support 24, according to the invention.

Figure 2:
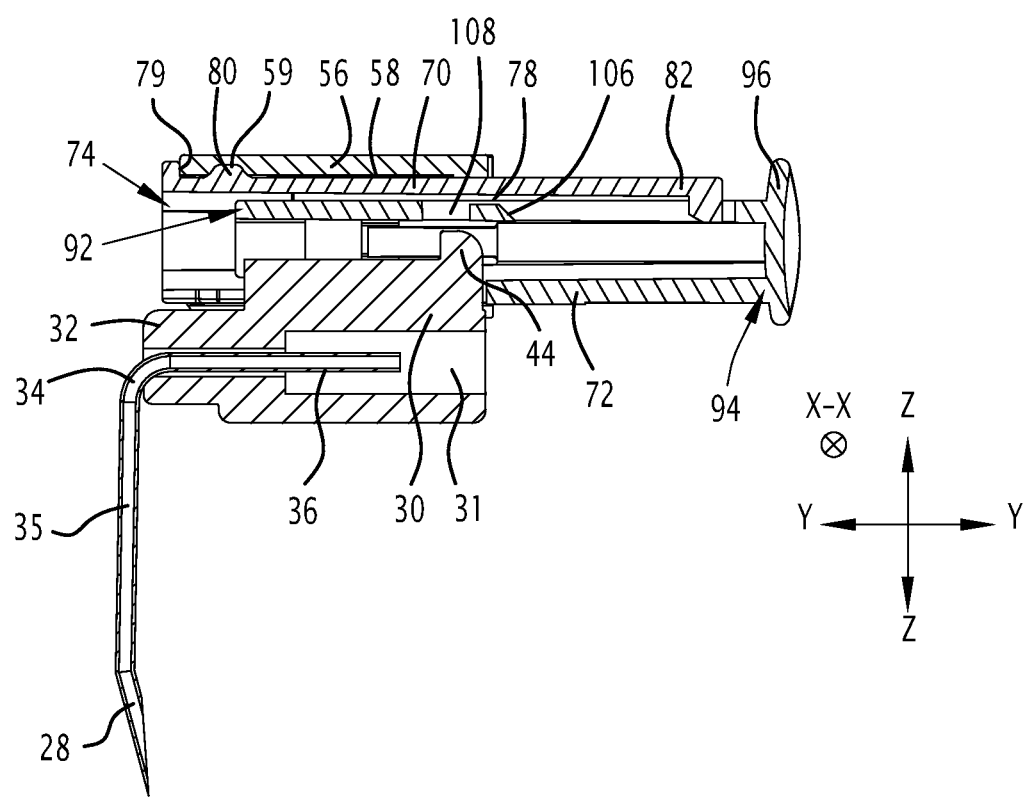
FIGS. 2 and 3 show longitudinal sectional views from the side and from above, respectively, of the device of FIG. 1.

The needle 22 extends substantially along an elevation axis Z-Z, as shown in FIG. 2.

The needle 22 has a curved tip free end 28, so that it opens laterally in relation to the elevation axis Z-Z.

The support 24 has a central core 30 elongated along a longitudinal axis Y-Y perpendicular to the elevation axis Z-Z. The central core 30 is substantially parallelepiped. It is crossed from one side to the other by a conduit 31 for conveying the liquid to the needle 22, extending along the longitudinal axis Y-Y. The needle 22 is attached to one end of the central core 30 that forms a head 32.

The needle 22 forms an elbow 34 (see FIG. 2), extending on the side of the free end 28 by a main section 35 extending along the elevation axis Z-Z, and by a connecting section 36 extending along the longitudinal axis Y-Y on the side opposite of the free end 28. The connecting section 36 is engaged in the axial duct passing through the central core 30, from the head 32.

The support 24 comprises two hinge pins 38, visible in FIG. 1, which project laterally on either side of the central core 30, near the head 32. The hinge pins 38 extend along a transverse axis X-X perpendicular to the elevation axis Z-Z and to the longitudinal axis Y-Y.

The support 24 further comprises two lower retaining pins 39 (one of which is visible in FIG. 6) and two upper retaining pins 40 (one of which is visible in FIG. 1), which project laterally from the central core 30, parallel to the transverse axis X-X.

The lower retaining pins 39 extend at the same level as the hinge pins 38 along the elevation axis Z-Z, from a portion of the central core 30 further from the head 32 along the longitudinal axis Y-Y.

The higher retaining pins 40 extend below the hinge pins 38 along the elevation axis Z-Z.

The lower retaining pins 39 and the higher retaining pins 40 have a lesser transverse extent than the hinge pins 38 along the transverse axis X-X.

On the side of the support 24 facing the needle 22, the support 24 has a support plate 42 extending along the length of the support 24. The head 32 projects from this support plate 42 along the longitudinal axis Y-Y.

On the side of the support 24 opposite the needle 22, the support 24 has a bar 44 for locking the extraction mechanism 50. The bar 44 extends above the central core 30 on the side opposite the head 32 along the longitudinal axis Y-Y. It projects laterally from both sides of the central core 30 in a direction parallel to the transverse axis X-X.

Figure 4:
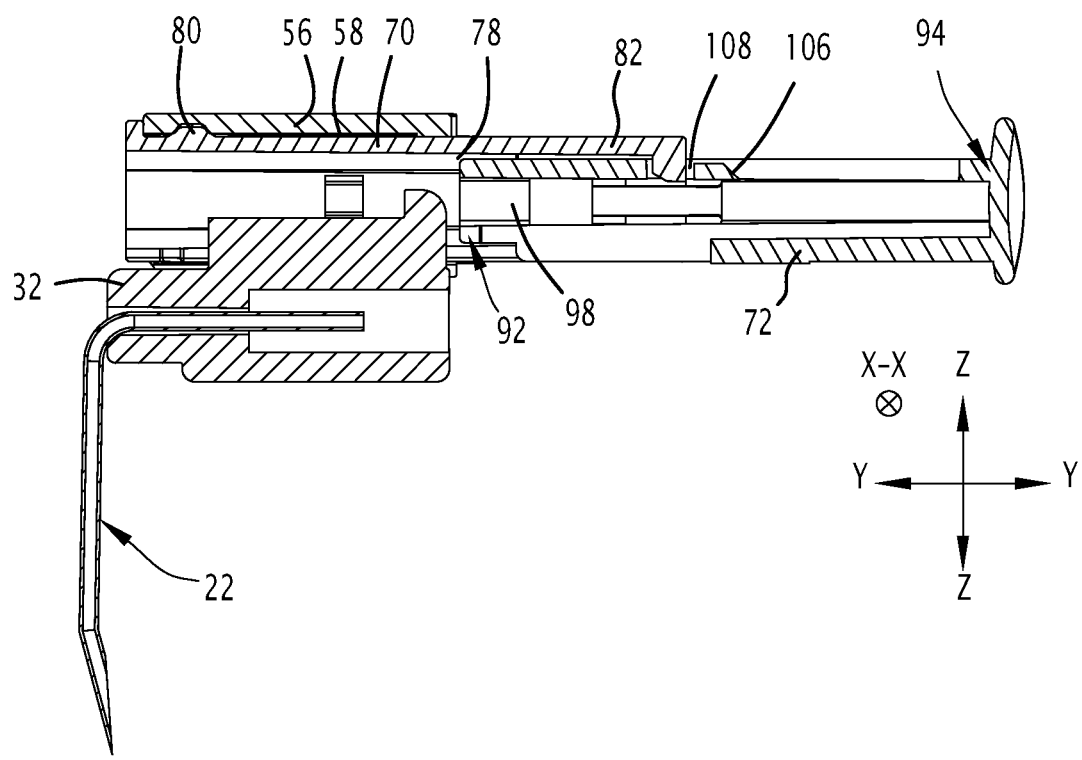
FIGS. 4 and 5 show longitudinal sectional views from the side and from above, respectively, of the device of FIGS. 1 to 3, with the plunger in the deployed configuration.
Figure 5:
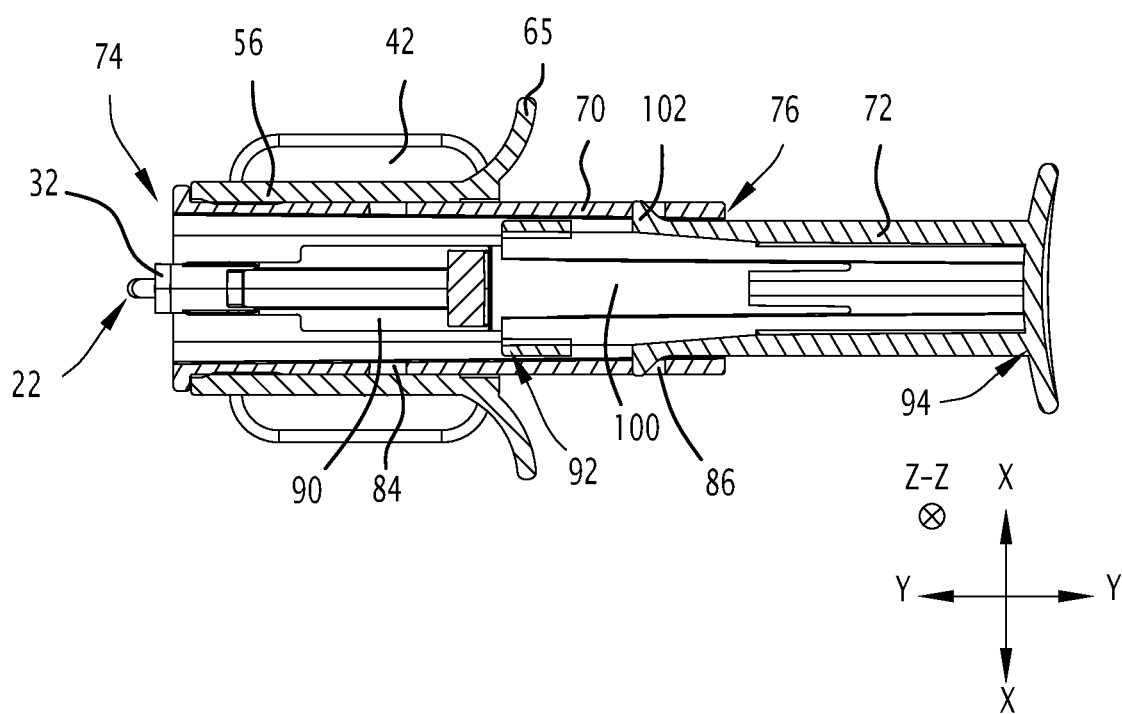
Figure 6:
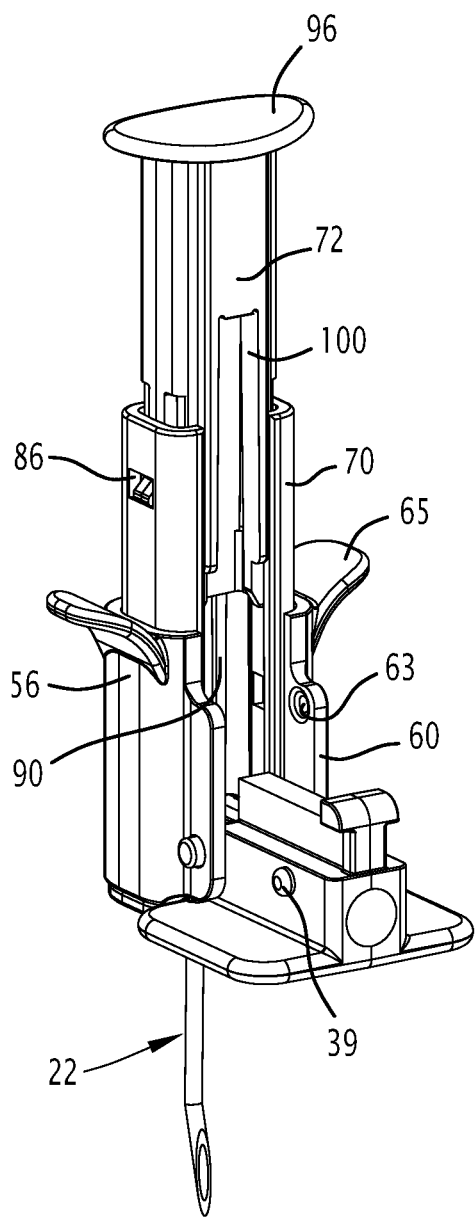
FIGS. 6 and 7 show rear three-quarter perspective and vertical cross-sectional views, respectively, of the device of FIGS. 1 to 5, with the extraction mechanism in the active configuration.
Figure 7:
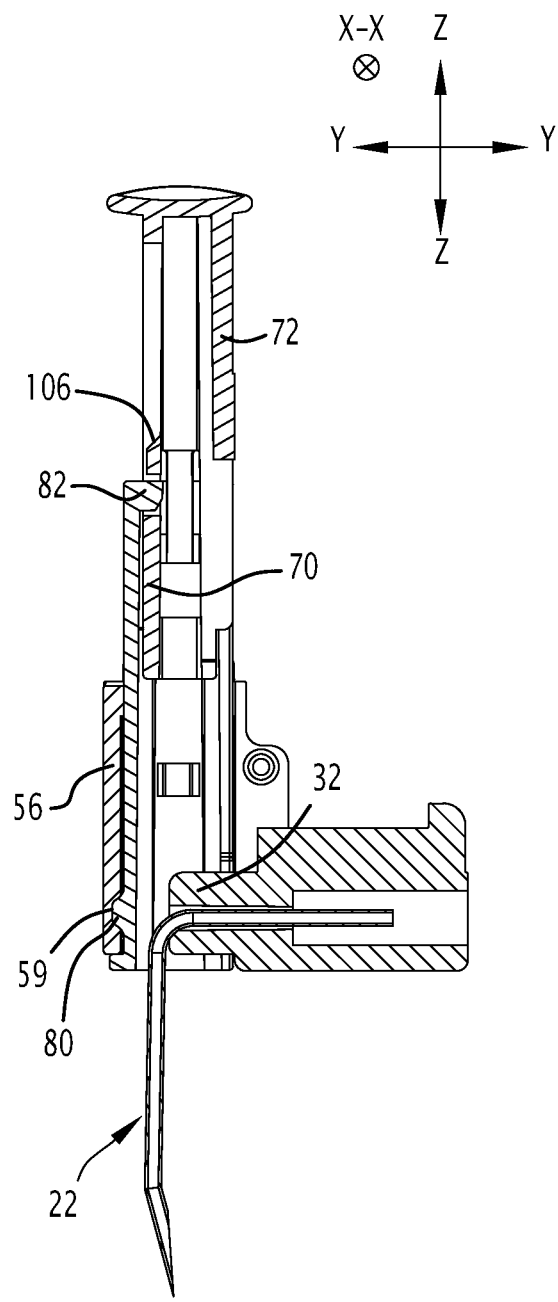
Figure 8:
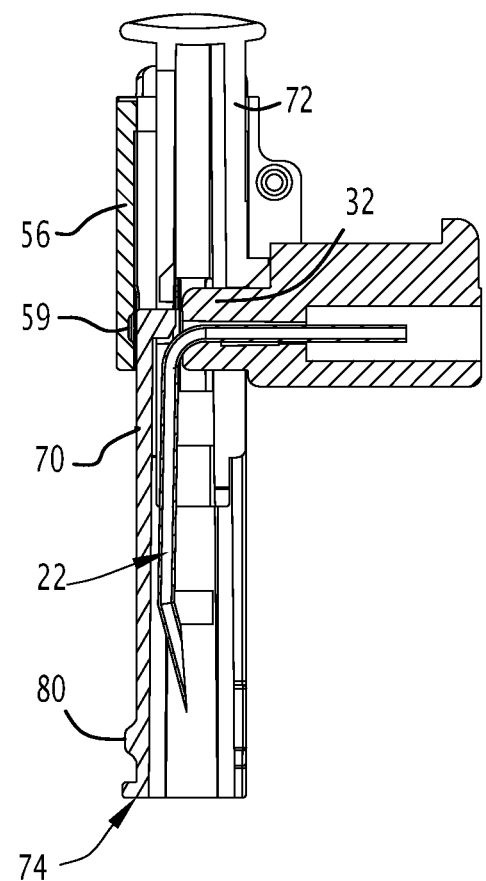
FIG. 8 is a vertical side section view of the device of FIGS. 1 to 7, in the needle extraction configuration.

The injection device 10 according to the invention comprises a needle 22 extraction mechanism 50 that is connected permanently to the needle support 24 and is movable relative to it, between an inactive extraction mechanism position, as illustrated in FIGS. 1 to 5, and an active extraction mechanism 50 position, as illustrated in FIGS. 6 to 8.

The extraction mechanism 50 includes a base 52 and a plunger 54, slidably mounted in relation to the base 52. The base 52 can be moved relative to the support 24 and in particular is articulated relative to the latter about the articulation pins 38.

The base 52 comprises a sleeve 56 delimiting a plunger 54 circulation passage 58.

When the extraction mechanism 50 is in the inactive position, the sleeve 56 extends substantially in a direction parallel to the longitudinal axis Y-Y.

When the extraction mechanism 50 is tilted to the active position, the sleeve 56 extends substantially in a direction parallel to the elevation axis Z-Z.

The sleeve 56 is open laterally over a width corresponding to the width of the central core 30 of the support. The sleeve 56 also defines a retaining cavity 59, opening into the internal passage 58, on its upper face.

The base 52 also comprises two flanks 60, extending the sleeve 56 on either side of this opening, suitable for engaging around the central core 30. The flanks 60 have two articulation holes 62 in which the articulation pins 38 are received, for articulation of the base 52 on the central core 30.

The articulation axis is parallel to the transverse axis X-X, in the vicinity of the head 32, so that in the tilted position, the head 32 extends into the passage 58, as shown in FIG. 7.

The flanks also have two lower retaining holes 63, visible in FIG. 7, and two upper retaining holes 64, visible in FIG. 1, opening onto the inner faces of the flanks 60.

The lower retaining holes 63 are adapted to receive the lower retaining pins 39 when the extraction mechanism 50 is in the inactive position, and thus allow temporary retention of the extraction mechanism 50 in the inactive position.

Similarly, the upper retention holes 64 are adapted to receive the upper retention pins 40 when the extraction mechanism 50 is in the active position, and thus allow temporary retention of the extraction mechanism 50 in the active position.

The base 52 further includes two lateral finger rests 65, projecting from the sleeve 56 at the end opposite the head 32.

The plunger 54 is received within the passage 58, slidable between a needle use position, as shown in FIGS. 1 through 7, and a needle extraction position, as shown in FIG. 8.

The plunger 54 comprises an outer member 70 mounted slidably in the base 52, and an inner member 72 slidably mounted in the outer member 70 in a telescoping manner with the outer member 70. The plunger 54 further includes a flexible interlocking mechanism.

The external member 70 is a hollowed-out sleeve with a cross-section complementary to that of the internal passage 58. This section is substantially rectangular with rounded corners.

The external member 70 is open at a front end 74 located close to the head 32, and at a rear end 76 located further from the head 32. The outer member 70 defines an interior passage 78 opening at the front end 74 and rear end 76.

The outer member 70 defines an outer shoulder 79 around its front end 74, and a retaining pin 80 protruding from a top face near the front end 74. The retaining pin 80 is suitable for insertion into the cavity 59 in the needle 22 use position. The outer shoulder 79 is adapted to rest against the front edge of the sleeve 56 when the retaining pin 80 is received in the cavity 59.

The outer member 70 defines an outer slot 90 oriented toward the needle support 24, open from the front end 74 to the rear end 76 and opening into the inner passage 78. The outer slot 90 has a width greater than the length of the bar 44.

The inner member 72 is a hollowed-out sleeve having a cross-section complementary to that of the inner passage 78. This section is substantially rectangular with rounded corners.

The internal member 72 has an open front end 92 and a rear end 94 provided with a rear finger rest 96. The internal member 72 defines an internal space 98, opening at the front end 92.

The inner member 72 further defines an internal slot 100, oriented toward the needle support 24. The internal slot 100 is open from the front end 92 to the rear end 94, and opens into the internal space 98. The internal slot 100 has a width that is less than the length of the bar.

The inner member 72 is mounted slidably in the inner passage 78 of the outer member 70 along a longitudinal axis of the plunger 54. The inner member 72 is thus movable from a retracted plunger 54 configuration, shown in FIGS. 1 through 3, and a deployed plunger 54 configuration, shown in FIGS. 4 through 8, in which the plunger 54 length is greater than in the retracted configuration.

When the plunger 54 is in the deployed configuration, the inner passage 78 of the outer member 70 and the inner space 98 of the outer member 72 form a continuous inner needle 22 receiving space defined by the plunger 54, as shown in FIG. 8.

The bar 44, the outer slot 90 and the inner slot 100 form a temporary immobilization assembly for the base 52 in the inactive position.

Figure 3:
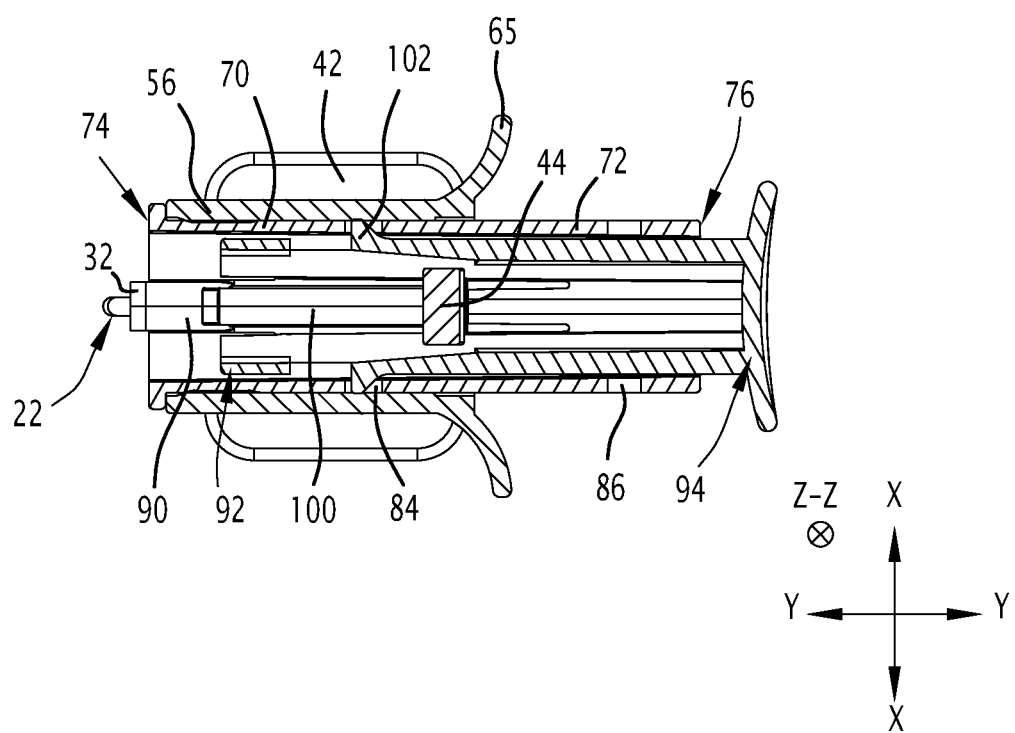

The temporary immobilization assembly is active when the plunger 54 is in the retracted configuration, as shown in FIG. 3. The bar 44 extends into the internal space 98, engaged through the outer slot 90 and the inner slot 100. Because the bar 44 length is greater than the inner slot 100 width, the bar 44 blocks movement of the plunger 54 away from the support 24. The base 52 is thus immobilized in the inactive position of the extraction mechanism 50.

The temporary immobilization assembly is deactivated when the plunger 54 moves from the retracted configuration to the deployed configuration, as shown in FIG. 5. In this configuration, the inner member 72 has moved along the longitudinal axis Y-Y away from the bar 44. The bar 44 is now only engaged in the outer slot 90, which is wider than the length of the bar 44. The base 52 can then be moved to the active position of the extraction mechanism 50.

The interlocking mechanism is suitable for locking the inner member 72 in its movement relative to the outer member 70 when the plunger 54 is in the deployed configuration.

The flexible interlocking mechanism comprises an upper snap-in tab 82 carried by the outer member 70 on an upper face at the rear end 76. The upper snap-in tab 82 carries a tooth at its free end facing the inner passage 78.

The flexible interlocking mechanism further comprises two lateral snap-in tabs 102 carried by the inner member 72 along two side faces, each lateral snap-in tab 102 carrying a tooth at a free end, facing outward. It comprises front housings 84 and rear housings 86 defined in side faces of the outer member 70, shown in FIGS. 3 and 5.

The teeth of the lateral snap-in tabs 102 are asymmetrical, i.e. they have a blocking side and a passing side. For example, the normal on the blocking side forms an angle of substantially zero with the lateral snap-in tab 102, while the normal on the passing side forms an angle of between 30° and 60° with the snap-in tab 102.

The flexible interlocking mechanism also includes a ramp 106, extending across an upper face of the inner member 72, and an upper housing 108, with the ramp 106 delimiting the upper housing 108 at its upper end.

In the deployed configuration, each of the teeth carried by the lateral snap-in tabs 102 is received by one of the rear housings 86, as shown in FIG. 5, and the tooth carried by the upper snap-in tab 82 is received by the upper housing 108, as shown in FIG. 4.

Advantageously, the flexible interlocking mechanism is suitable for temporarily retaining the inner member 72 in relation to the outer member 70 when the plunger 54 is in the retracted configuration.

Temporarily retaining means that the force required for the plunger 54 to leave the retracted configuration is sufficiently high for the plunger 54 not to leave the deployed configuration without manipulation by a user, but sufficiently low for such manipulation by the user not to cause jolts in the injection device 10 when the plunger leaves the retracted configuration. This force is advantageously between 6 N and 10 N.

In the retracted configuration, each of the teeth carried by the lateral snap-in tabs 102 is received by one of the front housings 84 defined by the external member 72. When the plunger 54 is moved from the retracted configuration to the deployed configuration, the passing side of each of the teeth rests on an edge of the front housing 84, allowing the tooth to move out of the front housing 84 when the user pulls on the inner member 72, with reduced effort required.

Conversely, when the plunger 84 is in the deployed configuration, each of the teeth carried by the lateral snap-in tabs 102 is received by one of the rear housings 86. The locking side of each of the teeth rests on an edge of the rear housing 86, preventing the tooth from moving out of the rear housing 86. The flexible interlocking mechanism thus resists movement of the inner member 72 away from the deployed configuration.

The method for operating the injection device 10, and more specifically for removing the needle 22, will now be described.

The injection device 10 is initially in the configuration shown in FIGS. 1 through 3, with the needle 22 passing through a patient's skin 12 to an implantable chamber 11 below. The support plate 42 is resting on the patient's skin.

The plunger 54 is in its retracted configuration and the extraction mechanism is in an inactive position. The plunger 54 extends substantially parallel to the longitudinal axis Y-Y.

The plunger 54 is in the needle 22 use position, with the shoulder of the front end 74 of the outer member 70 resting against the front of the sleeve 56, near the head 32. The retaining tab 80 is engaged in the retaining cavity 59 to hold the plunger 54 in the needle 22 use position.

The teeth of the side snap-in tabs 102 are engaged in the front housings 84, retaining the plunger 54 in the retracted configuration.

The bar 44 is located in the inner space 98 of the inner member 72, engaged in both the inner slot 100 and the outer slot 90, which are superimposed. Because the bar 44 length is greater than the width of the inner slot 100, the bar 44 completely locks the plunger 54 against the center core 30 and prevents the base 52 from tilting to the active position.

The plunger 54 length is minimized in the retracted configuration, reducing the device 10 encumbering the patient.

In a first step, the user pulls on the inner member 72 by the rear finger rest 96, so as to move the plunger 54 from its retracted configuration to its deployed configuration, shown in FIGS. 4 to 8.

The inner member 72 slides into the outer member 70 along the axis Y-Y. The plunger 54 length increases, so that it is more than 120% in the deployed configuration and preferably more than 125% of the retracted configuration length.

The teeth of the lateral snap-in tabs 102 extend from the front housings 84, then engage the rear housings 86 in the deployed configuration. The latch tooth travels along the ramp 106 and engages the upper housing 108 in the deployed configuration. The interlocking mechanism then locks the plunger 54 in the deployed configuration.

The bar 44 is released from the inner slot 100 and only engages in the outer slot 90. It no longer locks the plunger 54 against the center core 30. The bottom retaining pins 39 are engaged in the bottom retaining holes 63, and hold the base 52 in the inactive position.

In a second step, the user tilts the base 52 around the retaining pin from the inactive position to the active position. In the active position, shown in FIGS. 6 to 8, the plunger 54 extends substantially parallel to the elevation axis Z-Z.

The head 32 is then received in the inner passage 78. The top retaining pins 40 are engaged in the top retaining holes 64, so as to immobilize the base 52 in the active position.

In a third step, the user pushes on the rear finger rest 96 with the thumb while holding the side finger rests 65 with two other fingers, so as to slide the plunger 54 in the passage 58. The plunger 54 is then moved from a needle 22 use position, shown in FIGS. 6 and 7, to a needle 22 extraction position, shown in FIG. 8.

When moving from the needle 22 use position to the needle 22 extraction position, the retaining pin 80 is pushed out of the retaining cavity 59 by the user.

The shoulder of the front end 74 of the outer member 70 then rests on the patient's skin, providing a sufficient bearing surface, and the user pushing on the plunger 54 causes the base 52 to move up the plunger 54, extracting the needle 22 from the patient's body. The plunger 54 gradually swallows the needle 22.

In the needle 22 extraction position, the main section 35 of the needle 22 extends completely within the plunger 54 receiving space, with the front end 74 being beyond the free end 28. This protects the user by preventing any risk of accidental pricking.

It is conceivable that the extraction mechanism 50 takes up less space with such an injection device 10, especially when the plunger 54 is in the retracted position and has a reduced length. This reduces the space occupied by the injection device on the patient's skin, thus reducing the risks of handling errors during injection of the drug solution, as well as the risks of tipping caused by the pendulum effect of the plunger 54. The reduced size of the injection device 10 also improves patient comfort.

In addition, the device 10 comprises a flexible interlocking mechanism consisting of a plurality of snap-in tabs and related housings, which ensures that the plunger is securely locked in the deployed configuration to ensure efficient extraction.

Finally, the temporary immobilization of the base 52 in the inactive position combined with the temporary retention of the plunger in the retracted configuration by the flexible interlocking mechanism makes it possible to ensure that the base 52 and the plunger 54 remain inactive without external manipulation by an operator. This further reduces the risk of operator error.

The invention claimed is:

1. An injection device comprising:
 a needle support;
 an injection needle integral with the needle support and having a free end arranged away from the needle support; and
 an injection needle extractor comprising a base connected to the needle support and a plunger movable relative to the base between a needle use position and a needle extraction position, the base being movable relative to the needle support between an extractor inactive position and an extractor active position,
 the plunger comprising an outer member and an inner member movable relative to the outer member from a plunger retracted configuration to a plunger deployed configuration a length of the plunger in the plunger deployed configuration being greater than a length of the plunger in the plunger retracted configuration.

2. The device according to claim 1, wherein the inner member is slidably mounted in an inner passage of the outer member.

3. The device according to claim 1, wherein the plunger comprises a flexible interlocking mechanism configured to lock the inner member relative to the outer member when the plunger is in a deployed configuration.

4. The device according to claim 3, wherein the flexible interlocking mechanism comprises at least one snap-in tab held by one of the inner member or the outer member and at least one housing defined by an other of the inner member and the outer member, the at least one snap-in tab having at least one tooth received in the housing when the plunger is in the plunger deployed configuration.

5. The device according to claim 4, wherein the at least one housing is located near a first end of the other of the inner member or the outer member, so as to receive the at least one tooth when the plunger is in the plunger deployed configuration, the flexible interlocking mechanism further comprising at least a second housing located near a second end of the other of the inner member or the outer member so as to receive the at least one tooth when the plunger is in the plunger retracted configuration.

6. The device according to claim 4, wherein the flexible interlocking mechanism comprises a ramp extending over the other of the inner member and the outer member, the ramp delimiting one of the at least one housing at the top end of the ramp, the at least one snap-in tab bearing on the ramp when the plunger moves from the plunger retracted configuration to the plunger deployed configuration.

7. The device according to claim 3, wherein the flexible snap-in mechanism is configured to temporarily retain the inner member relative to the outer member when the plunger is in the plunger retracted configuration.

8. The device according to claim 1, wherein the plunger, in the plunger deployed configuration, defines a needle receiving internal space.

9. The device according to claim 1, comprising a base immobilizer configured to temporarily immobilize the base in the inactive position, the base immobilizer being active when the plunger is in the plunger retracted configuration and being deactivated when the plunger is moved from the plunger retracted configuration to the plunger deployed configuration.

10. The device according to claim 9, wherein the base immobilizer includes a first slot extending on the inner member and a second slot extending on the outer member, a width of the second slot being greater than a width of the first slot, the first slot and the second slots being oriented toward the needle support, the base immobilizer further comprising a bar configured to engage the first slot and the second slot, the bar having a length greater than the width of the first slot and less than the width of the second slot.

11. The device according to claim 1, wherein the inner member and the outer member have substantially rectangular cross-sections having rounded corners.

12. A method for preparing a removal of a needle previously inserted into a patient's body, implemented prior to the removal of the needle, the method comprising:
 providing a device according to claim 1, the base occupying the extractor inactive position, the plunger being in the plunger retracted configuration;
 moving the inner member relative to the outer member to move the plunger from the plunger retracted configuration to the plunger deployed configuration, to increase the length of the plunger;
 moving the base from the inactive position to the active position.

* * * * *